United States Patent
Rodiera Olivé et al.

(10) Patent No.: US 10,398,846 B2
(45) Date of Patent: Sep. 3, 2019

(54) MONITORING MANUALLY OPERATED SYRINGES

(71) Applicant: ROMALTEK MEDICAL, S.L., Barcelona (ES)

(72) Inventors: José Javier Rodiera Olivé, Barcelona (ES); Pau Soler I Pla, Barcelona (ES)

(73) Assignee: ROMALTEK MEDICAL., S.L., Barcelona (ES)

( * ) Notice: Subject to any disclaimer, the term of this patent is extended or adjusted under 35 U.S.C. 154(b) by 90 days.

(21) Appl. No.: 15/465,156

(22) Filed: Mar. 21, 2017

(65) Prior Publication Data
US 2017/0189621 A1    Jul. 6, 2017

Related U.S. Application Data

(63) Continuation of application No. PCT/EP2014/070220, filed on Sep. 23, 2014.

(51) Int. Cl.
*A61M 5/315* (2006.01)
*A61M 39/02* (2006.01)
(Continued)

(52) U.S. Cl.
CPC .... *A61M 5/31568* (2013.01); *A61M 5/31525* (2013.01); *A61M 5/31535* (2013.01);
(Continued)

(58) Field of Classification Search
CPC .. A61M 2005/1588; A61M 2039/0205; A61M 2039/0258; A61M 2039/0267;
(Continued)

(56) References Cited

U.S. PATENT DOCUMENTS

| 5,651,775 A | 7/1997 | Bradley et al. |
| 6,270,455 B1 * | 8/2001 | Brown ............... G16H 40/40 600/300 |

(Continued)

FOREIGN PATENT DOCUMENTS

| JP | 2011510749 A | 4/2011 |
| WO | 9803215 A1 | 1/1998 |

(Continued)

OTHER PUBLICATIONS

International Search Report in corresponding International Application No. PCT/EP2014/070220, dated Jul. 14, 2015.

*Primary Examiner* — Quynh-Nhu H. Vu
(74) *Attorney, Agent, or Firm* — Edell, Shapiro & Finnan, LLC

(57) ABSTRACT

A device for monitoring a manually operated syringe that according to one embodiment includes a basis which is adapted to be connected to a medication administration point of a patient and comprises a syringe insertion port to receive the syringe dispensing tip, the basis being configured such that when the syringe is inserted in the insertion port the syringe barrel is not in direct contact with the basis, and at least part of the syringe barrel projects from the basis in the direction of the barrel axis, and further comprising an image acquisition system arranged on the basis and adapted to capture an image of at least part of the syringe plunger when the syringe is inserted in the insertion port.

12 Claims, 6 Drawing Sheets

(51) Int. Cl.
*G02B 5/04* (2006.01)
*G02B 5/20* (2006.01)
*G06T 7/70* (2017.01)
*G06T 7/00* (2017.01)
*H04N 5/33* (2006.01)
*A61M 5/158* (2006.01)
*G06F 19/00* (2018.01)

(52) U.S. Cl.
CPC .... *A61M 5/31573* (2013.01); *A61M 39/0247* (2013.01); *G02B 5/04* (2013.01); *G02B 5/208* (2013.01); *G06T 7/0012* (2013.01); *G06T 7/70* (2017.01); *H04N 5/33* (2013.01); *A61M 5/158* (2013.01); *A61M 2005/1588* (2013.01); *A61M 2039/0205* (2013.01); *A61M 2039/0258* (2013.01); *A61M 2039/0267* (2013.01); *A61M 2039/0276* (2013.01); *A61M 2205/3306* (2013.01); *A61M 2205/52* (2013.01); *A61M 2205/6054* (2013.01); *A61M 2205/6063* (2013.01); *A61M 2205/6072* (2013.01); *A61M 2209/088* (2013.01); *G06F 19/3468* (2013.01)

(58) Field of Classification Search
CPC .. A61M 2039/0276; A61M 2205/3306; A61M 2205/52; A61M 2205/6054; A61M 2205/6063; A61M 2205/6072; A61M 2209/088; A61M 39/0247; A61M 5/158; A61M 5/31525; A61M 5/31535; A61M 5/31568; A61M 5/31573
See application file for complete search history.

(56) References Cited

U.S. PATENT DOCUMENTS

| | | | |
|---|---|---|---|
| 2001/0056258 A1 | 12/2001 | Evans | |
| 2002/0099334 A1 | 7/2002 | Hanson et al. | |
| 2006/0178578 A1* | 8/2006 | Tribble | B65B 3/003 600/432 |
| 2007/0239482 A1 | 10/2007 | Finn et al. | |
| 2009/0154789 A1* | 6/2009 | Wolfe | G01N 21/958 382/141 |
| 2009/0188311 A1 | 7/2009 | Cadieux et al. | |
| 2011/0112474 A1* | 5/2011 | Bochenko | A61M 39/02 604/68 |
| 2012/0268741 A1 | 10/2012 | Pommereau et al. | |
| 2014/0186935 A1* | 7/2014 | Yoo | G01N 35/00029 435/287.2 |
| 2016/0243314 A1* | 8/2016 | Rodiera Olive | A61M 5/31533 |

FOREIGN PATENT DOCUMENTS

| | | |
|---|---|---|
| WO | 2014023763 A1 | 2/2014 |
| WO | 2015062655 A1 | 5/2015 |

* cited by examiner

FIGURE 1a
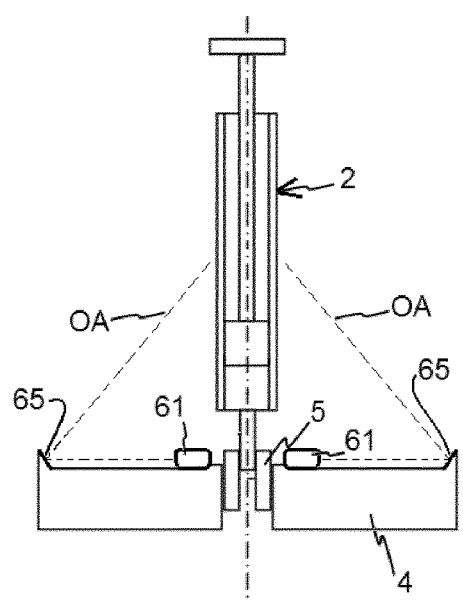
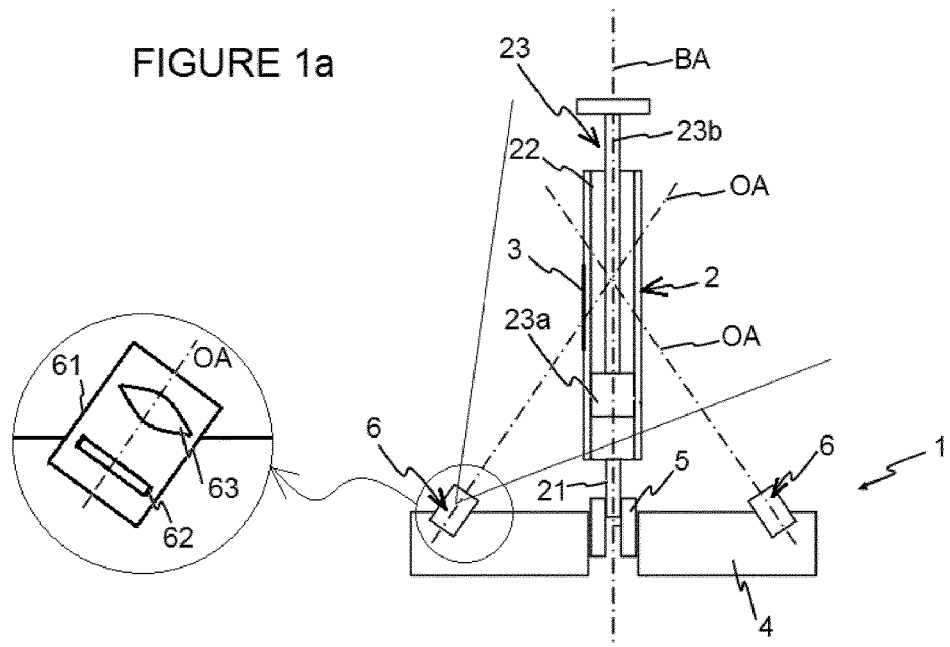
FIGURE 1b
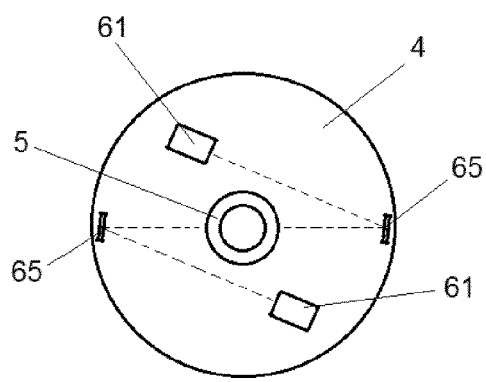
FIGURE 1c

MONITORING MANUALLY OPERATED SYRINGES

CROSS-REFERENCE TO RELATED APPLICATIONS

This application relates to and claims the benefit and priority to International Application No. PCT/EP2014/070220, filed Sep. 23, 2014.

FIELD

The present invention relates to a device and to a method for monitoring a manually operated syringe.

BACKGROUND

In a hospital environment patients may periodically be injected with medical drugs. In many cases such operations are performed manually; the recording and monitoring of medical drug administration to a patient is also usually performed manually, and therefore some operations might not be properly recorded.

For example, the stress conditions in operating rooms, ICU or emergency areas, and the consequent low priority of record keeping, may cause that a patient receives a medication but the information is not stored in the patient's medical record, or at least not stored with the desirable accuracy and detail.

On the other hand, monitoring the administration of drugs and storing the information for further reference are critical for a correct medical treatment.

An automatic medication delivery device is known for example from U.S. Pat. No. 5,651,775, which is able to monitor the drug delivery and record relevant events. This system involves placing the syringe in a cradle for the automatic delivery of the medication to the patient, and reading data from a special label associated with the syringe.

The placement of the syringe in a cradle limits the maneuverability of caregivers, and forces them to change the way they usually work; inserting the syringe in the device may also be time consuming. Furthermore, the cradle and the reading system don't allow using standard syringes and labels.

US2011/0112474 addresses the problem of manual record keeping, and discloses a medication delivery apparatus for use with a syringe. The syringe is provided with an information source that provides detectable information indicative of the medication in the syringe and/or the volume of its contents. The device has an identification sensor to detect the data on the information source, and a fluid delivery sensor.

However, according to this document sensors are arranged to read the area of the tip of the syringe, and therefore the information source must be placed in this area: this has several disadvantages, for example due to the small space available and the impossibility of using standard syringes and labels. Moreover, the fluid delivery sensor has a high cost and is prone to errors at different flow speeds.

It would be desirable to provide a device capable of monitoring a manually operated syringe while allowing the caregiver a significant degree of maneuverability, and generally reducing the drawbacks of the prior art.

SUMMARY OF THE DISCLOSURE

According to an aspect, the present disclosure relates to a device for monitoring a manually operated syringe, the syringe comprising a dispensing tip, a syringe barrel with a syringe barrel axis and a syringe plunger, and the device comprising: a basis adapted to be connected to a medication administration point of a patient and comprising a syringe insertion port adapted to receive the syringe dispensing tip, the basis being configured such that when the syringe is inserted in the insertion port the syringe barrel is not in direct contact with the basis, and at least part of the syringe barrel projects from the basis in the direction of the barrel axis; and an image acquisition system arranged on the basis and adapted to capture an image of at least part of the syringe plunger when the syringe is inserted in the insertion port.

The device allows the caregiver to rapidly insert a standard syringe in a standard access port and operate it manually in a comfortable way, with good visual access all around the syringe, and without worrying about writing down or storing the relevant data in the patient's record, because the device allows the automatic recording of the desired data from the syringe operation.

In particular, the image acquisition system adapted to capture an image of at least part of the syringe plunger when the syringe is inserted in the insertion port allows determining the plunger stroke during the manual operation of the syringe, and therefore the amount of delivered medication.

Consequently, the device may operate in a minimal invasive way to the practitioner; no change in current medical operations is needed. That is, the device is essentially transparent to the medical workflow.

The device may be embedded into a small apparatus that can be held close to the patient, much like a watch.

In some embodiments the image acquisition system is adapted to also capture an image of at least part of the syringe barrel when the syringe is inserted in the insertion port. This allows employing standard data labels that may be attached to the barrel.

According to another aspect, the present disclosure relates to a method for monitoring a manually operated syringe, comprising: providing a basis adapted to be connected to a medication administration point of a patient and comprising a syringe insertion port and an image acquisition system; detecting the insertion of a syringe in the insertion port; identifying the contents of the syringe; obtaining successive images of the syringe plunger; and processing the images to determine at least an initial plunger position and a final plunger position.

Additional advantages and features of embodiments will become apparent to those skilled in the art upon examination of the description, or may be learned by practice of the invention.

BRIEF DESCRIPTION OF THE DRAWINGS

Particular embodiments of the present invention will be described in the following by way of non-limiting examples, with reference to the appended drawings, in which:

FIG. 1a schematically shows an embodiment of a device for monitoring a manually operated syringe;

FIGS. 1b and 1c are schematic views of two embodiments of the arrangement of the image acquisition system on the basis;

DETAILED DESCRIPTION

Figure 2:
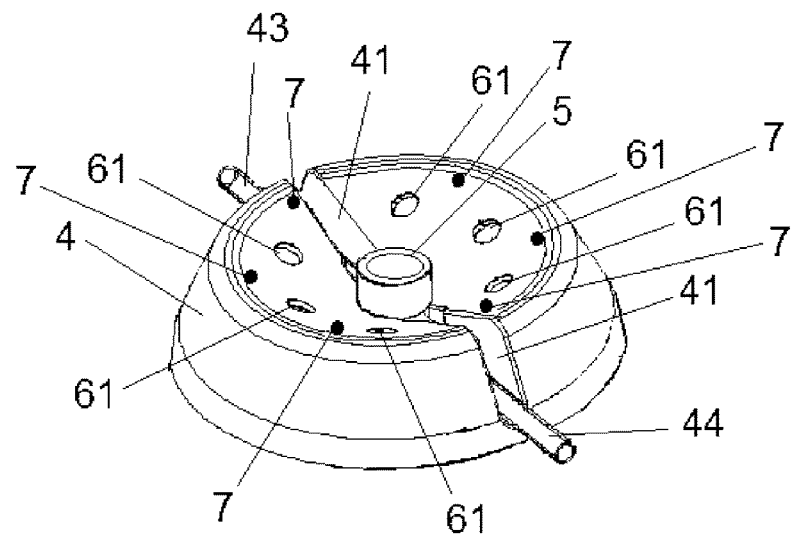
FIG. 2 is a perspective view of another embodiment of a device for monitoring a manually operated syringe.

In some embodiments, a device 1 for monitoring a manually operated syringe 2 comprises a basis 4 such as shown in FIG. 1, which is intended to be connected to a medication administration point of a patient. A syringe insertion port 5, for example a Luer port, is provided on the basis 4, for receiving the dispensing tip 21 of a syringe 2. The syringe 2 is shown with a data label 3 attached to it, in this case to the syringe barrel 22. The data label 3 may be a standard label as printed for human reading, and/or may contain a code, for example a bar code or QR code (Quick Response code) identifying inter alia the medication, syringe size, etc.

The basis 4 may be itself attached to the patient, for example taped to the skin or fastened by a strap, and the port 5 may be in fluid connection with e.g. an intravenous cannula (not shown) for intravenous infusion; but the basis 4 may also be placed near the patient, and the port 5 may be connected with a conduit of an intravenous infusion tubing set (Y-Set, T-Set, etc.), in such a way that a medication may be delivered to the patient from a manually operated syringe, using the port 5 in the device 1.

It will be understood that the device 1 may be portable, i.e. it may be hand held by the caregiver and attached to the patient as convenient.

As can be seen in the figure, the basis 4 is configured such that when a syringe 2 is inserted in the device at least part of the syringe barrel 22 projects from the basis in the direction of the barrel axis BA, and is not in direct contact with it. This means that the space surrounding the syringe barrel is free, so that the doctor, nurse or other caregiver that uses the device 1 to deliver medication manually to the patient from a syringe may comfortably control the operation he/she is performing, with enough space for the hand holding the syringe, and with a good vision of the syringe barrel from any angle.

The device 1 may also comprise an image acquisition system 6, arranged on the basis 4 in such a way that at least part of the syringe barrel 22 or of the syringe plunger 23 may be in the field of view of the imaging acquisition system 6 when the syringe is inserted in the insertion port. Consequently, the system 6 may be adapted to capture an image of at least part of the syringe barrel 22, or of the syringe plunger 23.

The device 1 may also comprise a control unit (not shown in FIG. 1) to control the operation of the image acquisition system 6 and to store and/or transmit to a computer system the generated images and/or data derived therefrom. For example, the device may be used to determine the length of the syringe plunger stroke in order to determine the amount of medication supplied to the patient, and/or to read an identification label attached to the syringe barrel to securely identify the medication that is being delivered, as will be explained with more detail later on.

It will therefore be appreciated that embodiments of the device allow a caregiver to easily insert a syringe 2 into the port 5 and manually deliver medication from the syringe to the patient, and during this operation the control unit may operate the image acquisition system 6 to automatically obtain images from the syringe barrel and/or syringe plunger, process them to obtain desired data, for example the medication being delivered, the delivered amount, etc., and finally store/transmit these data to a computer system.

In some embodiments, such as that of FIG. 1, the whole length of the syringe barrel 22 may project from the basis 4; however, the device 1 could also be designed such that only part of the barrel projects, for example at least half of the barrel, or at least one third of the barrel.

In some embodiments, an optical axis OA of the image acquisition system may intersect the syringe barrel axis BA at a point external to the basis 4, for example a point within the length of the barrel 22, such as shown in FIG. 1.

Since the image acquisition system 6 is arranged on the basis 4, generally in the vicinity of the syringe insertion port 5, in practice in such embodiments the optical axis OA of the system 6 will be inclined with respect to the syringe barrel axis BA and with respect to the surface of the barrel 22. That is, the optical axis OA will not intersect the barrel surface at right angles, as can also be seen in FIG. 1.

This means that no cameras or other elements need to be present at a substantial height above the basis 4, around the syringe barrel 22. This arrangement of the image acquisition system therefore allows leaving free space around the syringe barrel 22, facilitating the vision and the operations of the caregiver.

In some embodiments the optical axis OA of the optical system may be inclined an angle of between 30° and 90° with respect to the plane of the basis (i.e. with respect to a plane at right angles to the barrel axis BA).

By optical axis OA it is herein meant the axis of the optical path resulting from any arrangement of the image acquisition system 6, and not strictly the geometrical axis of a particular physical imaging device, which may be arranged in several ways on the basis.

In some embodiments the image acquisition system 6 may be at a distance of less than 20 cm from the insertion port 5; in some embodiments, this distance may be of less than 10 cm.

In simple embodiments the image acquisition system 6 may comprise for example a single unit 61, for example a camera or a video camera. An example of a suitable unit 61 is very schematically depicted in the enlargement of FIG. 1: the unit 61 may comprise a solid state sensor 62, such as a CCD or CMOS sensor, to record the image and an optical system 63, for example one or more suitable lenses, to focus the image of the syringe barrel 22 or plunger 23 on the sensor 62.

The image acquisition system 6 may also comprise several sensors and optical systems, arranged on the basis 4 and distributed around the insertion port 5. For example, the system may comprise several units 61, for example two of them, such as visible in FIG. 1, but also for example three, four, five or six units 61, or even more, arranged on the basis 4 around the port 5 such that each covers an angular portion of the syringe barrel 22.

In some embodiments, the optical distance between the imaging system and the syringe may be increased by arranging the units 61 on the basis 4 facing away from the syringe, and providing mirrors or reflecting prisms with the suitable inclination to deflect the optical path towards the syringe barrel.

FIG. 1b, for example, is a schematic partial elevation view showing a unit 61 arranged facing away from the syringe and a mirror 65 arranged at the periphery of the basis 4.

The units 61 may have their axis arranged in a radial direction on the basis 4, but they may also be arranged at an angle with respect to the radial direction, as shown schematically in the plan view of FIG. 1c, so as to further increase the length of the optical path. The plane of each mirror 65 is then inclined in two different directions (horizontally and vertically), as suitable to deflect the path towards the syringe.

FIG. 2 shows schematically in perspective an embodiment of the device 1 with an image acquisition system having six units 61 arranged in the basis 4, each comprising an optical system and a solid state sensor, distributed around the port 5. In the particular embodiment shown, the basis 4 has a channel 41 for housing tubes 43 and 44 of an intravenous infusion system, in communication with the syringe insertion port 5.

Figure 3:
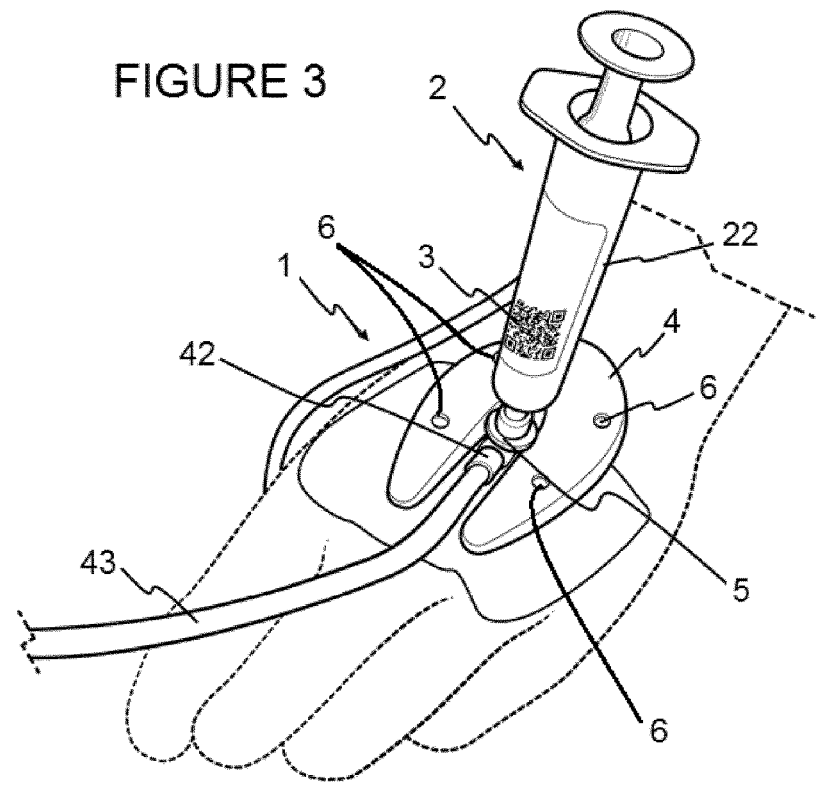
FIG. 3 shows a further embodiment of a device for monitoring a manually operated syringe.

FIG. 3 shows a further embodiment of the device 1, with an image acquisition 6 having four units distributed around the port 5 on a horseshoe-shaped basis 4. The device 1 is shown attached to the hand of a patient and with a syringe 2 inserted in the port 5. In the figure is also visible a connection port 42, which is in communication with the syringe insertion port 5 and with a tube 43 of an intravenous infusion system.

The use of multiple image acquisition units allows the caregiver more freedom to operate, because the syringe can be inserted in any position, and it also reduces the problems of reflection and improves the quality of the images, because it allows choosing the best view amongst those provided by the different units.

In relation with the image acquisitions system 6, the enlarged detail of FIG. 1 shows an embodiment of a unit 61 in which the sensor 62 and the optical system 63 are parallel to each other, and both are mounted inclined with respect to the plane of the basis 4, the plane of the sensor being perpendicular to the optical axis OA of the optical system. The basis may be considered to have an overall flat configuration, extending on a plane substantially at right angles to the axis of the port 5, that is, to the syringe barrel axis BA. However, in practice the basis may have a shape or configuration that is not flat or planar (e.g. it may be curved wholly or partially, have recesses and projections, etc.).

In alternative embodiments the image acquisition system 6 may comprise an optical system and a sensor that are not parallel to each other, in order to rotate the focal plane and improve the focus of the syringe barrel, in application of the Scheimpflug principle.

Figure 4A:
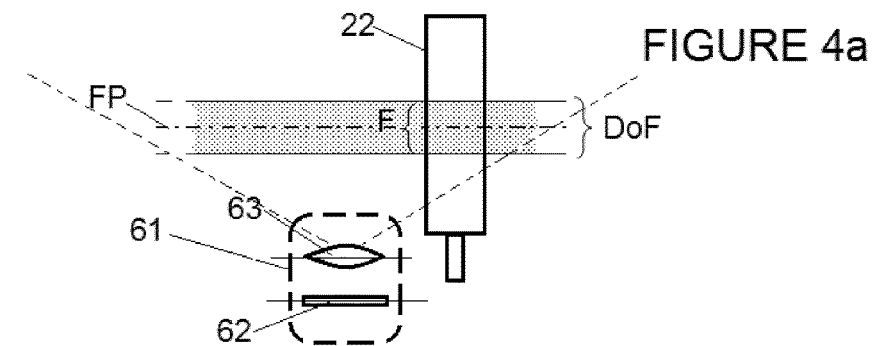
FIGS. 4a, 4b and 4c, 5a and 5b are schematic drawings illustrating how embodiments of the image acquisition system of the device capture an image of a syringe barrel.
Figure 4B:
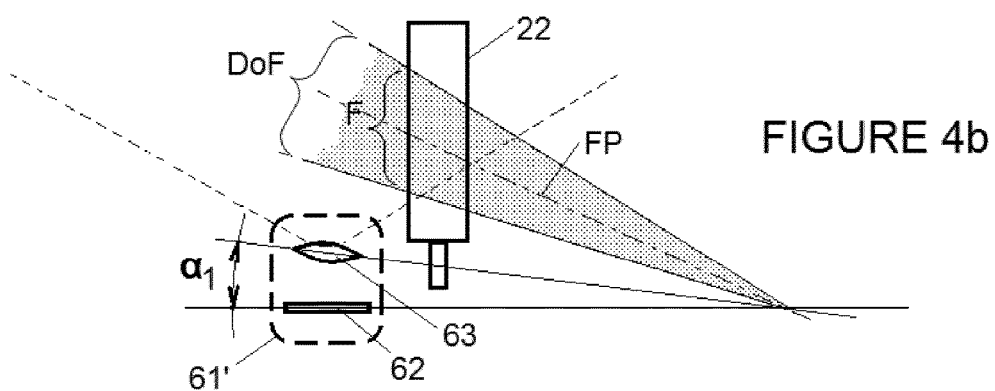
Figure 4C:
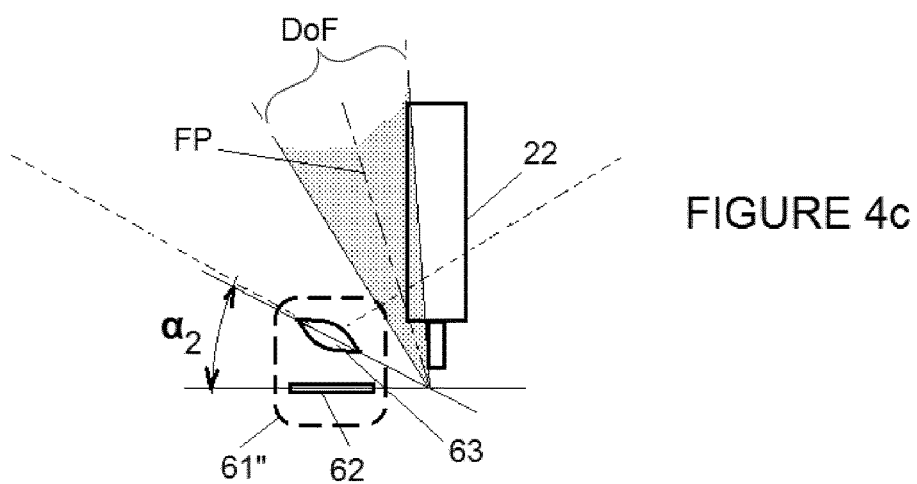

In order to illustrate the Scheimpflug principle, FIGS. 4a, 4b and 4c schematically show a syringe 2 and three embodiments of a camera or unit of the image acquisition system 6 arranged to have the syringe barrel in its field of vision. In FIG. 4a, the sensor 62 and the optical lens 63 of the unit 61 are parallel to each other, while in FIGS. 4b and 4c the plane of the optical lens 63 is tilted with respect to the plane of the sensor 62. The planes of the optical lens 63 and of the sensor 62 are represented by solid lines in these figures.

With the arrangement of FIG. 4a the focal plane FP of the optical system is parallel to the planes of the lens and the sensor, and the unit 61 obtains an image that is in focus within a depth of field zone DoF, between the two dashed lines shown at both sides of the focal plane in FIG. 4a. As can be seen, even if the whole of the syringe barrel 22 may be in the field of view of the optical system, only a short portion F of the height of the barrel will be reasonably in focus, while the image of the rest of the barrel will be blurred.

According to the Scheimpflug principle, if in a camera or unit 61' the plane of the lens 63 is tilted an angle $\alpha_1$ with respect to the plane of the sensor 62, the focus plane FP rotates and the depth of field zone DoF becomes wedge-shaped, as shown in FIG. 4b. The planes of the sensor and lens, the focal plane FP, and the planes limiting the depth of field zone DoF all intersect in a common point. As visible in FIG. 4b, in this case the portion F of the height of the barrel that will be reasonably in focus is larger than in FIG. 4b.

FIG. 4c shows a further embodiment of a camera or unit 61", in which the lens 63 is tilted an angle $\alpha_2$ larger than $\alpha_1$, and the focal plane is therefore further rotated, and as a consequence the whole of the syringe barrel lies within the depth of field zone DoF of the optical system.

Suitable tilting angles between the optical system 63 and the sensor 62 depend on the distance from the syringe insertion port 5, on the height of the syringe barrel, etc., and may be determined in each particular case. In some embodiments the tilting angle is at least 0.2°, for example between 0.2° and 15°. Tilting the optical system 63 with respect to the sensor 62 as shown in FIGS. 4b and 4c allows arranging the sensor 62 flat on the basis 4, which significantly simplifies the construction of the device (the CCD or CMOS can simply be welded on a printed circuit board in the basis 4), while still obtaining a focused image of the region of interest of the syringe barrel 22, and without affecting other optics parameters such as aperture and lens size.

In units such as 61, 61' or 62" of the image acquisition system 6 the optical system may also comprise a prism or the like in order to rotate the field of vision towards the syringe barrel 22.

Figure 5A:
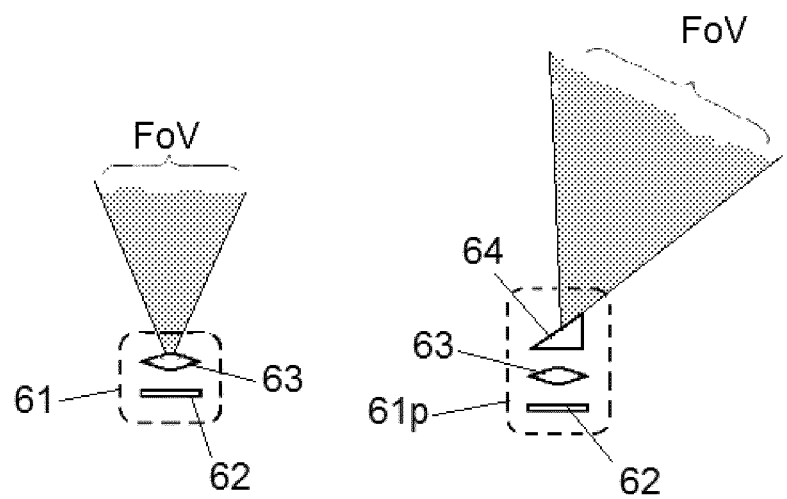

FIG. 5a schematically illustrates in the first drawing the field of vision FoV of a unit 61 such as that of FIG. 4a. In the second drawing, a unit $61_p$ may be provided with a prism 64, whereby the field of vision FoV is rotated, and may capture all the region of interest of the syringe barrel 22 (and plunger 23 if desired).

Figure 5B:
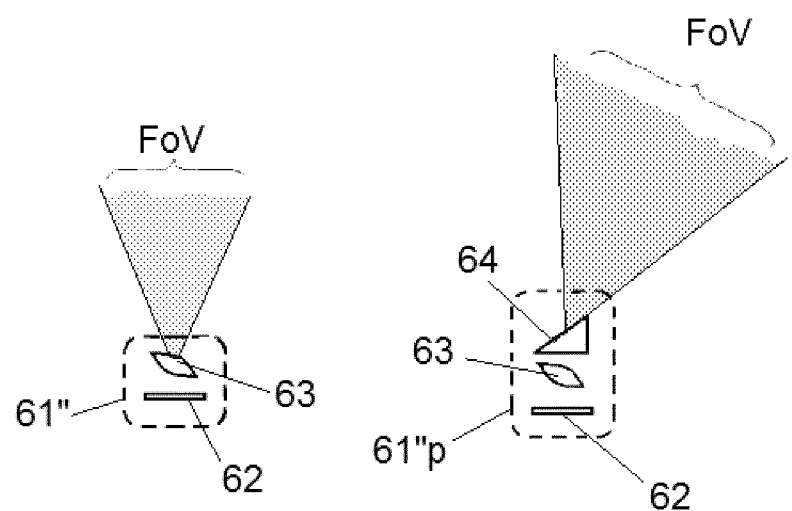

Similarly, FIG. 5b schematically illustrates in the first drawing the field of vision FoV of a unit 61" such as that of FIG. 4c. In the second drawing, a unit $61"_p$ may be provided with a prism 64 to rotate the field of vision FoV and capture all the region of interest of the syringe barrel 22 (and plunger 23 if desired). The prism angle may be between 0° and 45°, if a prism of plastic material is employed; a prism made of crystal, which has a larger refraction index with respect to plastic, may have smaller angle.

With cameras or units such as unit $61"_p$ which are provided with a prism 64 and a lens 63 that is tilted with respect to the sensor 62, it is possible to arrange the image acquisition system on the basis 4 and close to the syringe insertion port 5, such that the whole device may have a very reduced size, with the sensor 62 simply welded on a printed circuit board, while at the same time capturing good quality, focused images of the desired parts of the syringe 2.

The optical system may be manufactured as an integral unit comprising the optical prism and the lenses; for example it can be moulded in a single part.

In all cases, the optical system may comprise variable focus lenses to permit changing the position of the focal plane FP so that it can focus on the appropriate region. Lenses may also be designed to compensate for the geometric aberration: in particular, they can be designed with curved surfaces, and/or including a mirror to extend the field of view, i.e. to optically amplify regions that are more remote from the optical system and thus obtain an even resolution throughout the syringe barrel height.

The optical system may also be provided with a polarising filter to mitigate reflections, for example a linear or circular polarising filter.

In order to facilitate obtaining images of the syringe barrel or plunger, the device may comprise an illumination system 7, which may be arranged on the basis 4, to illuminate the syringe barrel 22 and/or syringe plunger 23 of a syringe 2 inserted in the insertion port, such that the image acquisition system does not need to rely on the environmental light. The illumination system 7 may comprise several light sources arranged on the basis 4, such as the six sources 7 shown in FIG. 2.

The light sources may be flashing light sources of high luminance and intensity: the high intensity improves the signal-to-noise ratio especially in the areas of the image where they may be reflections, and using flashing light sources allows providing high intensity light with reduced energy consumption. The operation of the flashing light sources may be synchronised with the operation of the image acquisition system. A flashing light source may comprise a light source and a flash controller to switch on and off the source as needed.

In some embodiments of the device, the light sources may be IR LEDs, or other infrared light sources; since IR light is invisible to the human eye, this prevents the illumination system from bothering the caregivers, even if flashing and/or high luminance sources are used. When IR light sources are employed, the image acquisition system may be provided with corresponding IR filters.

The light sources may also be polarised, with the image acquisition system being provided with matching polarising filters.

In some embodiments the illumination system 7 may include light sources arranged to illuminate the liquid inside the syringe barrel 2, as this may enhance the contrast of the image and therefore improve the images that may be obtained. In some embodiments a light source, such as for example a green or red laser source, may be directed from the basis 4 of the device towards the lower part of the side wall of the syringe barrel 22, or towards the bottom of the barrel 22. This provides enhanced contrast between the liquid and the plastic components of the syringe 2.

In addition to the image acquisition system 6, the device 1 may also be provided with an RFID (Radio Frequency Identification) sensor, suitable for detecting an RFID label that is associated with a syringe, as will be described later on.

In some embodiments the device 1 may be made up of both reusable and disposable parts: for example, the basis 4 with the image acquisition system 6, the illumination system 7, etc. may be reusable, while the port 5 and the tubing, and any other parts that may be in contact with liquids, may be disposable. To this end, the basis 4 and the port 5 may be adapted so that the port can be removed from the basis, for example pressure fitted.

Devices such as disclosed in the above embodiments may be used to monitor a syringe that is manually operated by a caretaker to supply medication to a patient. A method for monitoring such a syringe may for example comprise the steps of:

providing a device 1 such as disclosed above;

detecting the presence of a syringe 2 in the insertion port 5;

identifying the contents of the syringe, for example by detecting a data label 3 attached to the syringe barrel 22;

obtaining images of the plunger 23 in different positions of its travel along the barrel 22; and processing the images to determine the length of the plunger stroke during the operation of the syringe 2 by the caretaker, between an initial plunger position and a final plunger position, to enable determining the volume of medicament delivered by the syringe 2; and storing the obtained information, and/or transmitting it to an external computer system.

In order to determine the length of the plunger stroke, images may be taken of the plunger tip portion 23*a*, through the transparent wall of the barrel 22, or of the portion of the plunger stem portion 23*b*, when it is outside the barrel 22. The stem portion 23*b* may be provided with marks to facilitate detection of the position of the stem portion 23*b*; similarly, the tip portion 23*a* may be configured to offer good contrast within the barrel 22.

Figure 6A:
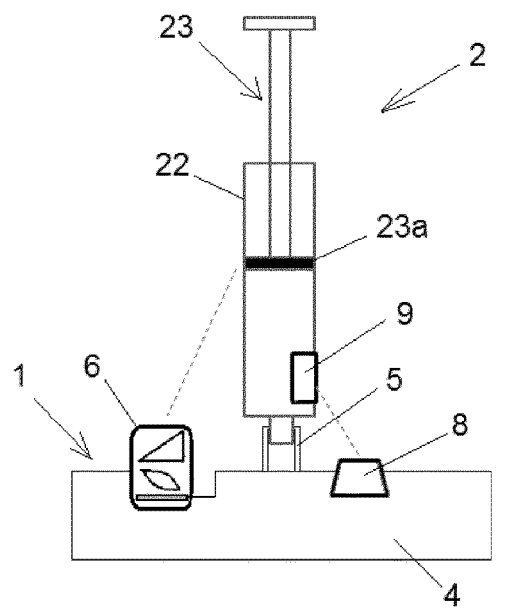
FIGS. 6a, 6b, 7, 8a and 8b are diagrams for illustrating embodiments of a method for monitoring a syringe.
Figure 6B:
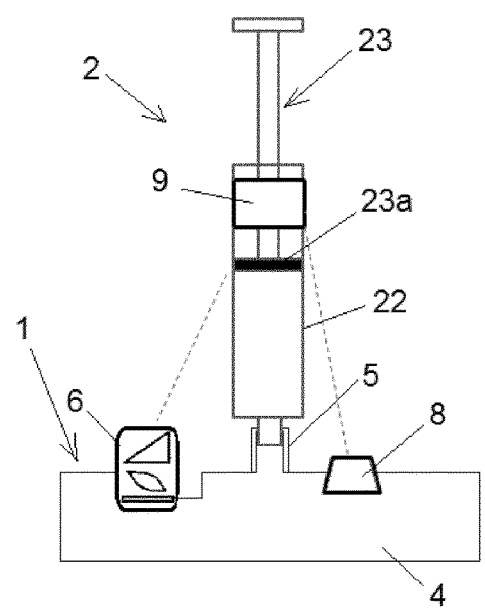

In embodiments of the method, such as shown in FIGS. 6*a* and 6*b*, the image acquisition system may be arranged to track the plunger stroke to allow determining the volume of medication delivered, while the identification of the syringe and of the medication may be done by an RFID system.

In FIG. 6*a*, an RFID sensor 8 is provided on the basis 4, and may detect a RFID label 9 attached to the lower part of the syringe barrel 22. Alternatively, such as shown in FIG. 6*b*, the RFID label 9 may be attached to the upper part of the syringe barrel 22.

In FIGS. 6*a* and 6*b* the image acquisition system 6 may comprise a single unit or camera, which captures images of the plunger tip portion 23*a* through the transparent wall of the barrel 22. The syringe 2 may be inserted in the port 5 in a suitable position such that the RFID label 9 doesn't obstruct the field of view of the camera.

Figure 7:
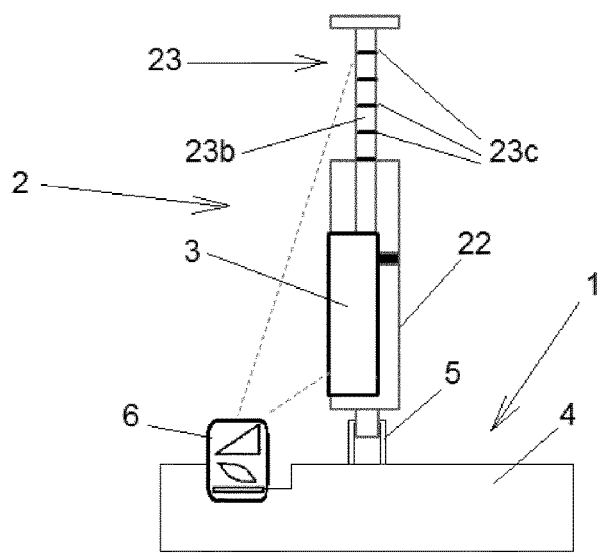

FIG. 7 illustrates an embodiment in which a single unit or camera of the image acquisition system 6 may be arranged to capture images of the portion of the plunger stem portion 23*b*, when it is outside the barrel 22, and also images of a QR label 3 or similar data label, attached to the barrel 22. The plunger stem portion 23*b* may comprise marks 23*c* to facilitate tracking its position with the camera. In alternative embodiments, the QR label 3 may be replaced with an RFID label, and the device 1 may be provided with a RFID sensor such as described in relation to FIGS. 6*a* and 6*b*, such that the camera only needs to capture images of the plunger.

Figures 8A, 8B:
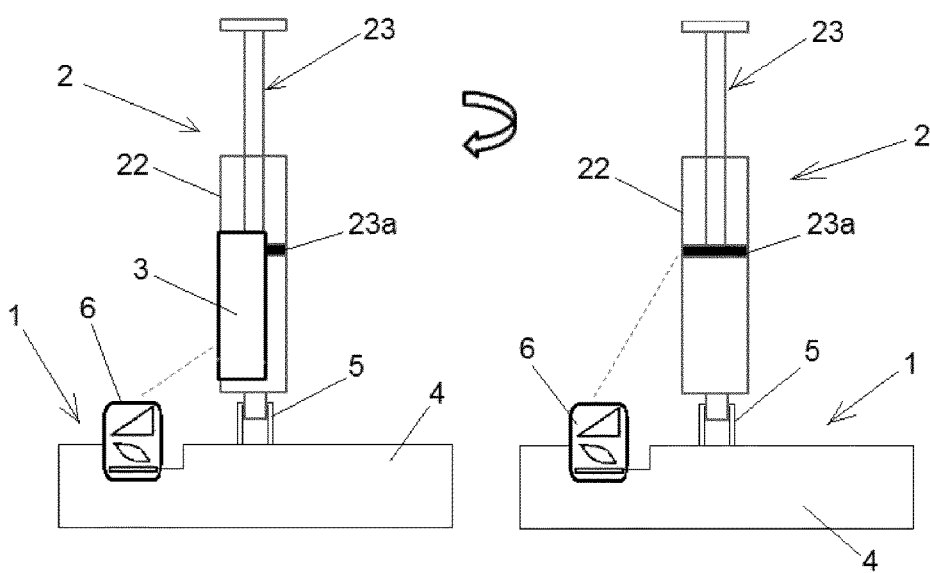

In other embodiments, as shown in FIGS. 8*a* and 8*b*, the system relies on the operator to rotate the syringe, so that first the ID data label 3 is scanned by the camera (FIG. 8*a*), and then the operator rotates the syringe in the port 5 so that the plunger position may be scanned by the camera. Medical staff is already familiar with this operation, since it is common in Luer lock syringes.

The syringe insertion port 5 may comprise a seat (not shown) in which the syringe tip may be inserted and rotated throughout an angle.

In embodiments of the device 1 with several units or cameras, such as that depicted in FIG. 3, in which the cameras are employed both for reading a label 3 with a QR code and for determining the stroke of the plunger, the method may involve:

detecting the presence of a syringe 2 in the port 5;

capturing video images with all the cameras simultaneously or in sequence, in such a way that images from all angles are captured, while firing light flashes from the illumination system;

analysing the video streaming of all the units until the QR code of the label 3 is detected;

storing the QR code;

analysing the video streaming of all the units to locate the image of the plunger 23;

determining from this analysis the initial and final positions of the plunger; and determining the amount of delivered medication from the length of the plunger stroke and the size of the syringe.

Having views from several cameras permits both convenience to the user and robustness to the operation, to avoid obstructions and reflections.

Once the initial position of the plunger is determined, the system may issue a signal (sound, light, illumination, ... ) to inform the caretaker that he/she may start the injection, and then the system may go on to analyse the video streaming from the cameras to detect the final position of the plunger.

The initial position may be determined as the first position in which the system has identified the plunger, and the final position may be determined as the last position in which the system has identified the plunger (which will generally be just before the syringe is removed from the device).

As a safety measure to avoid errors in the final position of the plunger if the system can no longer identify the plunger e.g. due to image recognition issues, it may be foreseen that the system attempts to read again the syringe label when it cannot detect the plunger: if the label is detected, showing the syringe is still present in the port 5, the system continues trying to detect a final position of the plunger.

In the following some further details regarding the QR code detection and the determination of the volume of administered medication are explained; it will be understood that they may be applied to multiple embodiments of the method. Further details regarding particular techniques and mathematical functions that are mentioned may be found in specialised handbooks.

Detection of the Plunger and Determination of the Administered Volume

As explained above, the amount or volume of administered medication may be calculated from the length of the plunger stroke and the size of the syringe (diameter of the syringe barrel).

The size of the syringe barrel may be obtained from the QR code or other identification label; the length of the plunger stroke may be determined by detecting the plunger positions during its movement using the image acquisition units or cameras and digital processing of the images.

Optical flow techniques may be used to detect the plunger: optical flow consists in detecting object movements within a video sequence, e.g. computing the correlation of different blocks of interest within the image.

The search of movements within the image is limited in this case to the object of interest (the plunger), which may be identified with the help of several features, such as:

Shape: the plunger will have a certain side ratio and width, depending on the plunger position and syringe size.

Orientation: the plunger will be positioned perpendicular to the side of the syringe barrel.

Size: the plunger will have a size within a predetermined range, depending on the plunger distance from the camera to the syringe.

Colour: the plunger will typically be black or white, making it easier to discriminate from other objects such as fingers, etc.

Movement direction: the movement of the plunger is clearly defined, as it will be contained within the syringe barrel and in the direction to push the liquid out of the syringe, so the search of movement will be limited to this direction.

These criteria may therefore be used to identify the plunger in its movement and discriminate from other spurious movements, such that the robustness of the image processing method is increased.

Given the proposed geometry of the plunger, a height-dependant pattern matching algorithm may be implemented, in which pattern matching of the plunger with a template or prefixed shape based on the above-mentioned characteristics varies as function of the image height. Pattern matching of the actual plunger image and the template can be measured by means of Cross Correlation, or by Normalized Mutual Information (NMI).

The process may be performed with each camera, and each may lead to an initial and a final position of the plunger. Each video sequence provides a figure of confidence, which depends from the correlation found between the detected object and the prefixed shape, where higher correlation implies higher confidence: in some cameras there will be little confidence in the measure, as there might be occlusions, while others might give a very reliable measure.

The final determination or estimation of the initial and final position of the plunger, and therefore of the plunger stroke and of the volume of administered medication, will be obtained applying an algorithm, e.g. by the average weighted by the confidence of the individual measures, or by selecting the camera with the best view (highest confidence).

Identification of the Syringe and/or Substance

The identification of the syringe and/or the substance or medication contained in the syringe may be done by several methods: for example, by reading a printed label that encodes the relevant information on the substance and/or the syringe itself (QR code, bar code, ... ), or an RFID encoded label, which may be applied on the syringe barrel. In other embodiments the identification may be done by analysing the substance (e.g. using a spectrophotometer), or simply by providing pre-programmed data in the system.

In some embodiments, the relevant information for identification of the syringe/substance is provided in a QR code printed on a label. QR standard is described in ISO/IEC 18004. In such cases, the steps involved in the identification of the syringe and/or the substance may be as described below:

Acquisition: acquisition of a video stream from each camera of the image acquisition system.

Preliminary detection: from the video stream, a region of interest where the QR code is located can be detected by use of local statistics, in particular local histogram and variance, to identify a region of black and white patterns, i.e. patterns that look like a QR code. This method has the advantage of being invariant to scale and translations, and accelerates the operation by focusing on the region of interest only.

Geometrical transformation: given the cylindrical shape of the syringe barrel where the label with the QR code is applied, and the close distance of the camera, acquired images may present a geometrical distortion, and in some cases it may be convenient to correct this distortion of the rounded shape of the QR code. In such cases, the change of coordinates can be performed through B-spline interpolation, using the fixed QR patterns as corresponding landmarks.

Alternatively, the QR codes could be printed in a way that the distortion induced by the image capture is minimized.

Once the image has been geometrically corrected through the coordinate change, the Hough Transform can be used to accelerate edge detection.

Code extraction: the process for extraction of the QR code from the image depends on whether the QR code is in the field of view of a single camera (in the case of systems with a single camera, and also in the case of systems with several cameras), or it is spread across different cameras, each seeing only a part of the QR code.

If the whole QR fits into the field of view of a single camera, the detection procedure may be as described in Section 13 of the ISO/IEC 18004 standard; if the QR is spread across different views, alignment marks can be used as references to extract a part of the code that is visible on each camera.

Fiducial marks can be introduced in the label to help guide the detection of the QR label. In particular a red dashed line can be drawn around the QR label to help guide detection.

Detection of the Presence of the Syringe

Before the identification of the syringe/substance, and/or the detection of the plunger are performed, the operation of the device may involve detecting the presence of a syringe.

This may be done by several different methods; in particular, the same image acquisition system may be employed to detect the presence of a syringe by pattern matching, for example by filter detection of borders, by blob analysis, either shape or orientation, by thresholds of such quantities, by line detection (also through the Hough Transform), etc. Alternatively, sensors, such as IR detectors or photocells, can be added to the hardware design to detect the syringe presence.

In all cases, the images may be processed by the control unit of the device, or by a unit external to the device itself, for example belonging to a hospital computer system. The control unit may store and/or transmit through any known protocol (bluetooth, etc.) the information of the injection that is performed on the patient, such that this information may be automatically stored in the patient's history.

Furthermore, during the operation the system may provide information to the caretakers, for example through a screen and/or by an acoustic system: the system may issue a signal e.g. when the QR code has been detected, and/or when the initial/final positions of the plunger have been detected, and/or when it is unable to obtain an image, etc. The system may allow the injecting operation by the caretaker even if it is unable to read the QR code and/or the plunger position.

Although only a number of particular embodiments and examples of the invention have been disclosed herein, it will be understood by those skilled in the art that other alternative embodiments and/or uses of the invention and obvious modifications and equivalents thereof are possible. Furthermore, the present invention covers all possible combinations of the particular embodiments described. Thus, the scope of the present invention should not be limited by particular embodiments, but should be determined only by a fair reading of the claims that follow.

What is claimed is:

1. A device for monitoring a manually operated syringe, the syringe comprising a dispensing tip, a syringe barrel with a syringe barrel axis and a syringe plunger, the device comprising:
    a basis configured to be connected to a medication administration point of a patient and comprising a syringe insertion port configured to receive the syringe dispensing tip, the basis being configured such that when the syringe is inserted in the insertion port the syringe barrel is not in direct contact with the basis, and at least part of the syringe barrel projects from the basis in the direction of the barrel axis, and
    an image acquisition system arranged on the basis and configured to capture an image of at least part of the syringe plunger when the syringe is inserted in the insertion port, the image acquisition system comprising a solid state sensor and an optical system configured to focus an image of the syringe barrel on the solid state sensor, the optical system comprising an optical prism.

2. The device according to claim 1, wherein the imaging acquisition system is configured to also capture an image of at least a part of the syringe barrel when the syringe dispensing tip is inserted in the insertion port.

3. The device according to claim 1, wherein an optical axis of the image acquisition system intersects the syringe barrel axis at a point within the barrel when the syringe is inserted in the insertion port.

4. The device according to claim 1, wherein the optical system is aligned on a first plane and the solid state sensor is aligned on a second plane, the first plane being tilted with respect to the second plane.

5. The device according to claim 4, wherein the first plane is tilted with respect to the second plane by an angle of between 0.2° to 15°.

6. The device according to claim 1, wherein the image acquisition system comprises at least two sensors and at least two corresponding optical systems, the at least two sensors and at least two corresponding optical systems being arranged on the basis and distributed around the insertion port.

7. The device according to claim 1, further comprising an illumination system adapted to illuminate the syringe barrel when the syringe is inserted in the insertion port.

8. The device according to claim 7, wherein the illumination system comprises a light source arranged on the basis.

9. The device according to claim 7, wherein the light source is an infrared light source, and the optical system comprises an infrared filter.

10. The device according to claim 7, wherein the illumination system is configured to illuminate a liquid in an interior of the syringe barrel when the syringe dispensing tip is inserted in the insertion port.

11. The device according to claim 1, wherein the image acquisition system is configured to capture an image of a data label attached to the syringe barrel when the syringe dispensing tip is inserted in the insertion port.

12. The device according to claim 1, wherein the image acquisition system is configured to capture images of the syringe plunger at different positions when the syringe dispensing tip is inserted in the insertion port.

* * * * *